United States Patent [19]
Wecke

[11] Patent Number: 5,400,796
[45] Date of Patent: Mar. 28, 1995

[54] DEVICE FOR IDENTIFYING ATRIAL DEPOLARIZATION

[75] Inventor: Liliane Wecke, Sundbyberg, Sweden

[73] Assignee: Siemens-Elema AB, Solna, Sweden

[21] Appl. No.: 139,834

[22] Filed: Oct. 22, 1993

[30] Foreign Application Priority Data

Oct. 28, 1992 [SE] Sweden .................. 9203171

[51] Int. Cl.6 .......................... A61B 5/0464
[52] U.S. Cl. .................. 128/705; 128/696; 128/702
[58] Field of Search .......... 128/702, 696, 705, 706, 128/708; 607/9, 14

[56] References Cited

U.S. PATENT DOCUMENTS

| | | | |
|---|---|---|---|
| 4,539,991 | 9/1985 | Boute | 607/9 |
| 4,572,192 | 2/1986 | Jackman et al. | 607/14 |
| 4,624,260 | 11/1986 | Baker, Jr. et al. | 607/14 |
| 4,712,554 | 12/1987 | Garson, Jr. | |
| 4,723,551 | 2/1988 | Hedberg et al. | |
| 4,788,980 | 12/1988 | Mann et al. | 607/14 |
| 4,917,115 | 4/1990 | Flammang et al. | |
| 4,974,589 | 12/1990 | Sholder. | |
| 5,010,887 | 4/1991 | Thornander. | |

FOREIGN PATENT DOCUMENTS

WO92/13596 8/1992 WIPO.

Primary Examiner—William E. Kamm
Assistant Examiner—Kennedy J. Schaetzle
Attorney, Agent, or Firm—Hill, Steadman & Simpson

[57] ABSTRACT

A device for identifying an event, among atrial events sensed in a heart, as an atrial depolarization includes an atrial detector which emits a first signal when an event is sensed in the atrium, and a ventricular detector which emits a second signal when an event is sensed in the ventricle. A window generator creates a time window with the first signal inside the window, and a comparator determines whether the second signal is inside or outside the window. If the second signal is outside the window, an identification signal for the atrial depolarization is emitted. In subsequent circuits in the device, an event sensed in the atrium can be indicated as e.g. atrial flutter or a crosstalk QRS. The indications can be used for controlling a heart stimulator. A corresponding method is also disclosed.

32 Claims, 3 Drawing Sheets

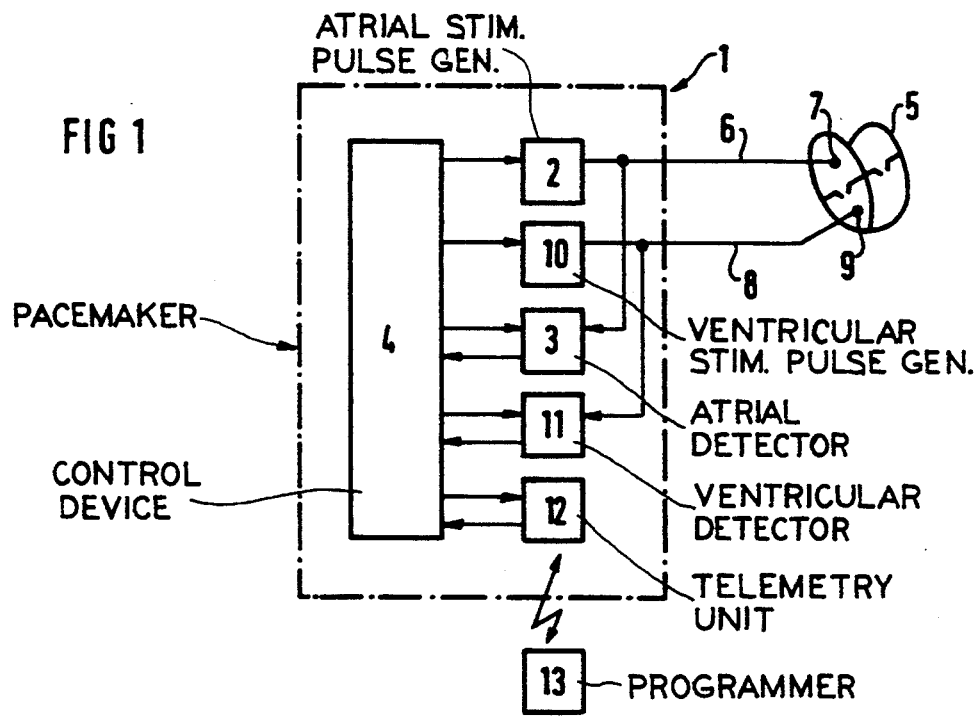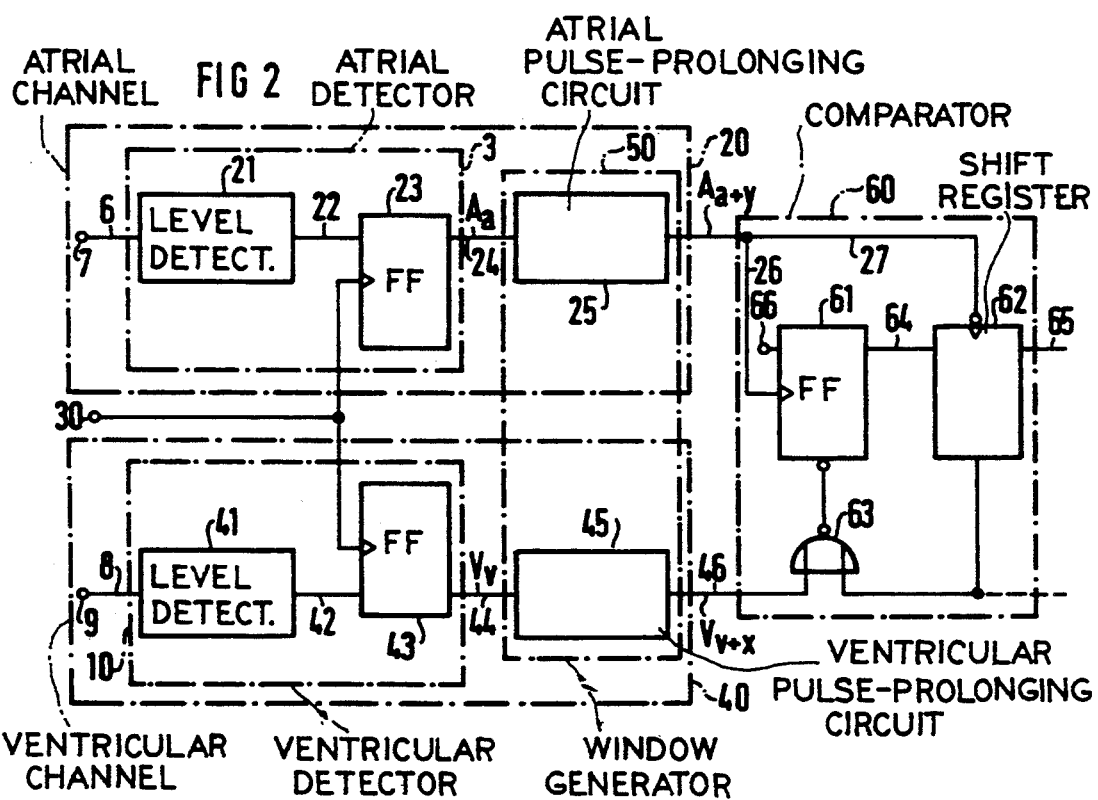

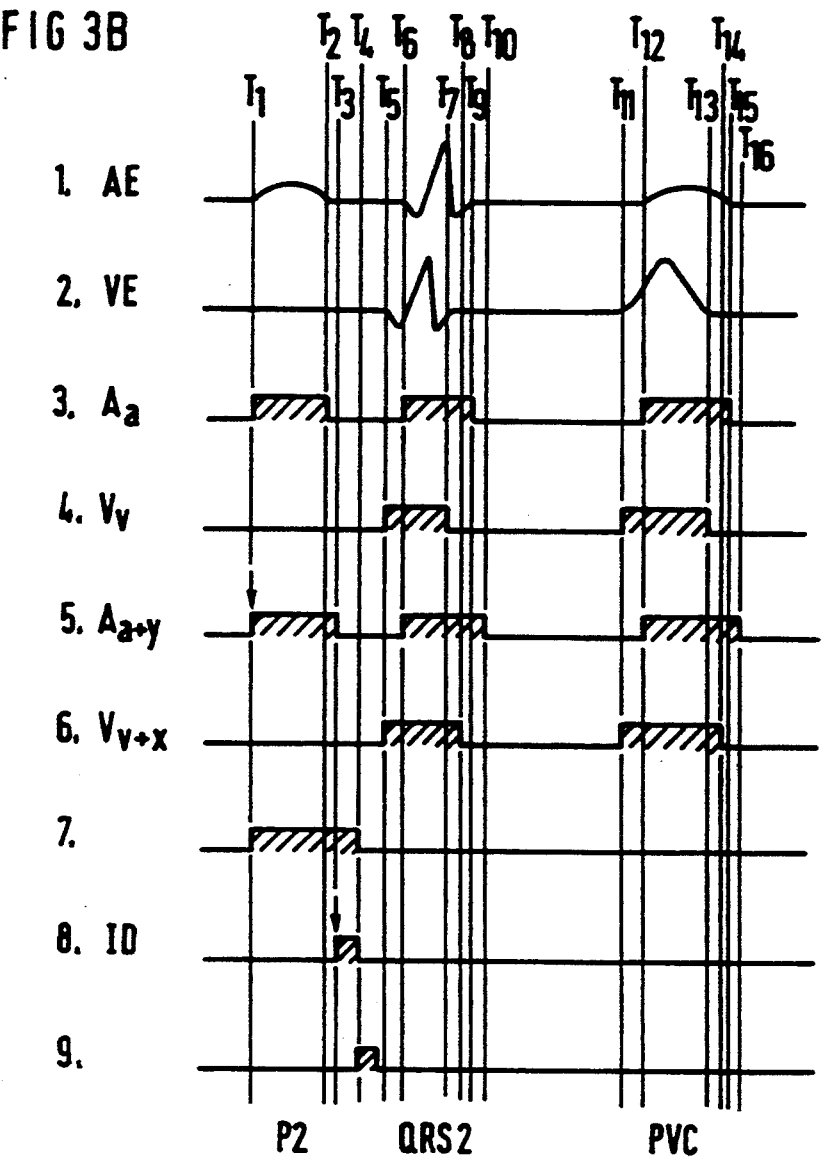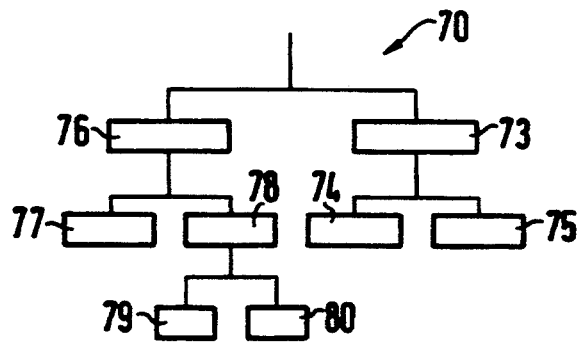

DEVICE FOR IDENTIFYING ATRIAL DEPOLARIZATION

BACKGROUND OF THE INVENTION

1. Field of the Invention

The present invention relates to a device and method for identifying an event, among events detected in the atrium in a heart, as an atrial depolarization.

2. Description of the Prior Art

An atrial depolarization manifests itself as a P wave when cardiac activity is recorded in an ECG. The corresponding depolarization in the ventricle gives rise to a QRS complex or an R wave in the ECG. In, e.g., physiological studies or in the treatment of the heart with an electrical heart stimulator such as a defibrillator, pacemaker etc., reliable identification of an atrial depolarization among events sensed in the atrium is important in many cases.

Reliable identification of the P wave is a problem, however, as illustrated below with an example from dual-chamber pacing. A dual chamber pacemaker can operate in different modes, usually designated with a three-position alphabetic code in which the first letter indicates stimulation in the atrium (A), ventricle (V) or both (D), the second letter indicates sensing in the atrium (A), ventricle (V) or both (D) and the third letter indicates the pacemaker's operating mode, i.e. triggered (T), inhibited (I) or both (D). For simplicity, these alphabetic designations will be used where appropriate in the description below, the letter A thus generally designating the atrium.

Thus, a dual chamber pacemaker operating in the DDD mode stimulates and senses in both the atrium and the ventricle, and its mode is either inhibited or triggered as needed. In the inhibited mode, the pacemaker's stimulation pulse is suppressed in the case of the atrium when a P wave is sensed, and in the case of the ventricle when a QRS complex or R wave is sensed. In other words, the pacemaker only stimulates if the heart's intrinsic signals are not sensed at the right time.

The correct operation of such a dual chamber pacemaker obviously depends on the ability of the pacemaker's sensing electronics to accurately sense the P wave for the atrium (atrial channel) and the R wave for the ventricle (ventricular channel), respectively. This cannot always be reliably accomplished because of interference, and pacemaker operation can then be affected. Sources of interference may be both inside and outside the heart and can affect sensing in both the atrial channel and the ventricular channel.

Since the present invention is for achieving reliable identification of the P wave, only interference problems in the atrium/atrial channel will be exemplified below.

One problem in the sensing of the P wave is caused by the circumstance that the QRS complex or R wave generated by the ventricle has an amplitude greatly exceeding the amplitude of the P wave. Thus, when crosstalk occurs in the heart, the R wave causes detection of a spurious P wave in the atrium with an amplitude which is equal to or often greater than the amplitude of the true P wave. Here, "crosstalk" means that the R wave is propagated to the atrium by electrical conduction in blood and tissue and sensed there by the pacemaker's sensing electronics for the atrium, i.e. far-field sensing of the R wave. The propagation time for the R wave in this context is on the order of 10 milliseconds. (For clarity, it should be noted that R wave crosstalk should be distinguished from retrograde conduction of the R wave to the atrium. In retrograde conduction, the myocardium's cells depolarize, and propagation time is on the order of 100 milliseconds. Retrograde conduction can also give rise to spurious P waves, but this phenomenon will not be discussed here.) A spurious P wave occurring in crosstalk can cause the pacemaker to mistakenly emit a stimulation pulse in the ventricle at a time corresponding to its repolarization, since the spurious wave occurs at a time corresponding to the R wave and not to atrial depolarization. In repolarization, which causes a T wave in the ECG, the ventricle is sensitive (the vulnerable phase) to electrical stimulation, and a pacemaker pulse delivered to the ventricle at this time could induce tachycardia or, at worst, fibrillation. These conditions are capable of causing cardiac arrest.

As noted above, other sources of interference can cause problems in the sensing of the P wave. Interference generated by, e.g., external electrical equipment can, through far-field sensing, cause spurious P wave sensing. Susceptibility to spurious P wave sensing related to far-field sensing depends on electrode placement in the atrium. The risk of spurious P wave sensing is particularly great if a separate electrode, affixed to the wall of the atrium, is not used for sensing, as can occur in the VDD mode (when the atrium is only sensed, not stimulated), but the electrode cable, whose tip is in the ventricle, is instead provided with electrode surfaces for sensing in the atrium, these electrode surfaces located so that a "floating" electrode results, i.e. the electrode is freely immersed in the blood of the atrium.

The prior art discloses a number of ways to avoid identification of spurious P waves as genuine. A spurious P wave often has, e.g., a different frequency content or appearance (morphology) from a genuine P wave. Filtering or some other form of signal processing have thus been used for discriminating spurious P waves. ECG signals, however, do not have the same morphology in different patients. This is because of the differing size and shape of the heart and/or differing placement of electrodes in different patients. In addition, ECG signals from the same patient may have different morphologies at different times because of, e.g., different transient pathological conditions in her/his heart and/or medication given to treat these conditions. In a heart, VES Ventricular extrasystoles which are fed back to the atrium, also have a morphology which greatly differs from a normal QRS complex. As a result of these variations in ECG signals, properly set sensing electronics, operating with filtration or morphology-processing signal conditioning capable of reliably identifying a genuine P wave on a particular occasion in a particular patient, may be totally incapable of achieving this identification in the same patient, or in another patient, on another occasion.

Another known way to avoid the sensing of spurious P waves is to impose a PVARP (post-ventricular atrial refractory period) with a duration suitable for the atrial channel's sensing electronics, after a spontaneous or stimulated QRS complex is sensed in the ventricle. The PVARP is achieved by blanking, i.e., the atrial channel's electronics are made insensitive by, e.g., cutting off the supply of power thereto. A blanking interval should be selected which is so long that atrial events capable of triggering stimulation in the ventricle during the vulnerable phase cannot be sensed. However, the interval must not be too long, since enough time must be left for the electronics to sense any genuine P wave for inhibition of the pacemaker before the pacemaker, in the DDD mode, triggers an atrial stimulation. The choice of an appropriate or optimum length for the blanking interval is often unfortunately associated with difficulties similar to those in the above described morphological and filtering techniques and therefore depends on both the choice of patient and the individual patient's condition on a particular occasion. In recent years, attempts have been made to resolve the difficulty in finding an optimum interval by introduction of a two-part blanking interval for the electronics, the first part of which an absolute refractory period (initial blanking interval) and the second part a relative refractory period, the blanking interval restarting if a signal is sensed during the relative refractory part of the blanking interval. This technique, in which prolongation of the blanking interval can be achieved up to a certain period of time after blanking is instituted the first time, is described in U.S. Pat. No. 4.974.589.

SUMMARY OF THE INVENTION

It is an object of the present invention to provide a method and apparatus for identifying the occurrence of an atrial depolarization, among a number of events in a heart, which has improved reliability in comparison to known detection and identification techniques.

The above object is achieved in accordance with the principles of the present invention in a method and apparatus wherein a first signal, such as from an atrial detector, is emitted upon the detection of an event in the atrium, a second signal is emitted, such as from a ventricular detector, upon the detection of an event in the ventricle, a time window is created with the first signal inside the window, and a comparison is undertaken which compares the second signal to the time window. A signal identifying the first signal as arising due to atrial depolarization is emitted if the second signal, as a result of the comparison, is determined to be not inside the window.

By making a check to ascertain whether a simple logical condition has been met for a signal from the atrium and a signal from the ventricle, the above-described problems are avoided as regards the PVARP and variations in ECG morphology.

The invention is based on the awareness that information which is available, or which can easily be obtained in a heart stimulator of the above-described type, can be utilized for identifying atrial depolarization or the P wave.

A signal from an event sensed in the atrium, which can consist of a P wave, a QRS complex from the ventricle or some other electrical event, is compared in a procedure described below to a possible signal from the ventricle. If there is only a signal from the atrium at the time of this comparison, the signal represents a P wave. When there are concomitant signals from the atrium and the ventricle, the signal from the atrium represents a QRS complex. When there are a plurality of consecutive signals from both the atrium and the ventricle, the atrial signal represents external interference.

The device may be used in a heart stimulator, operating according to the inventive method which can then be controlled to stimulate the heart in an appropriate way. If the heart stimulator is operating in the bradycardia-treatment mode, it can, e.g., be inhibited when a QRS complex is present, stimulate in the ventricle with a suitable delay when a P wave is present and stimulate at a fixed rate when external interference is present. If the heart stimulator is in the tachycardia-treatment mode, it can, when P waves occur at an interval which is shorter than a defined interval and this interval, e.g., serves as the criterion for atrial flutter or fibrillation, emit tachycardia-terminating stimulation pulses.

DESCRIPTION OF THE DRAWINGS

FIG. 1 shows a block diagram of a dual chamber pacemaker in which a detection device in accordance with the invention can be employed.

FIG. 2 shows, in a block diagram, a detection device according to the invention in a dual chamber pacemaker.

FIGS. 3A and 3B illustrate, in the form of a time diagram, the operation of the device according to FIG. 2.

FIG. 4 shows a flow chart, in accordance with the invention, of a function in the pacemaker's control device for evaluating the duration of intervals between certain emitted signals shown in FIGS. 3A and 3B.

DESCRIPTION OF THE PREFERRED EMBODIMENTS

Figure 3A:
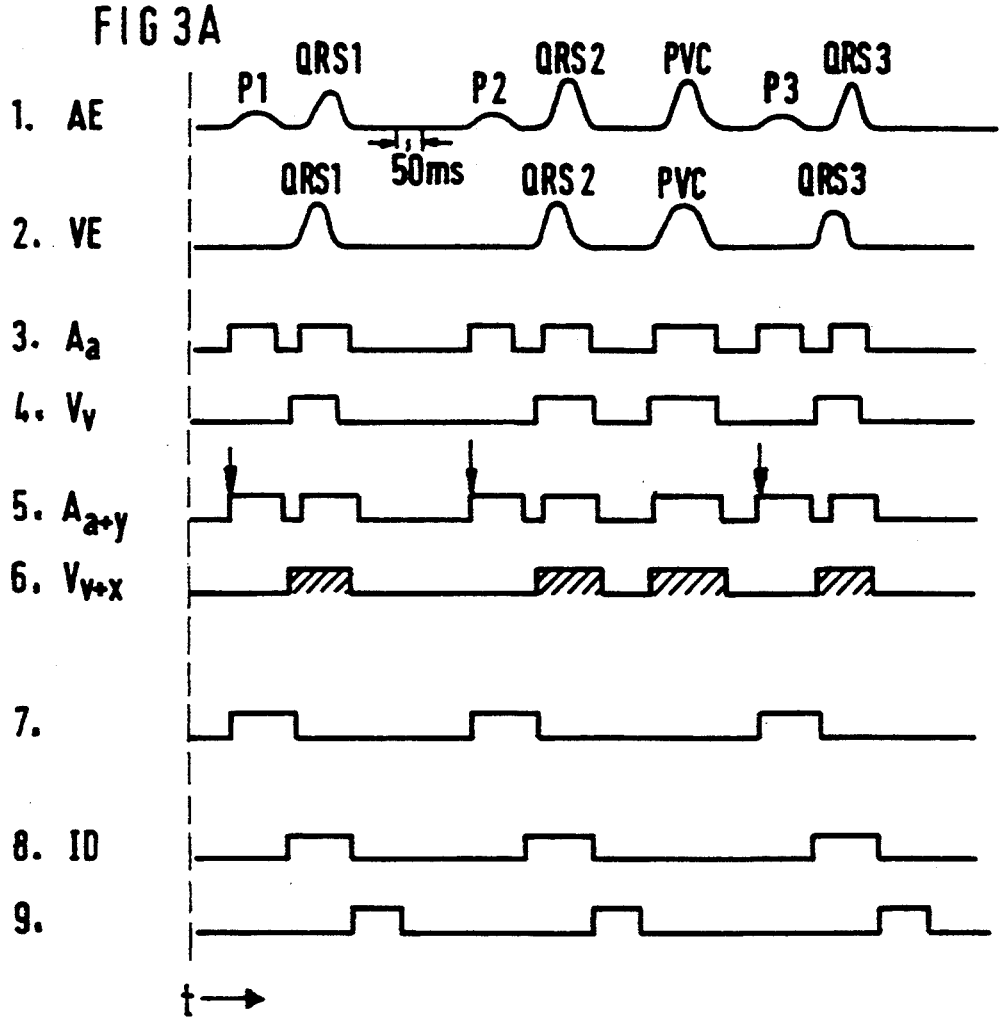

FIG. 1 is a block diagram of a dual chamber pacemaker 1 in which the device according to the invention can be used. The dual chamber pacemaker 1 contains an atrial stimulation pulse generator 2, an atrial detector 3, a ventricular stimulation pulse generator 10, a ventricular detector 11, a control device 4 and a telemetry unit 12. The atrial stimulation pulse generator 2 generates stimulation pulses, delivered to the atrium in a heart 5 via an atrial lead 6 and an atrial electrode 7 arranged thereon. The ventricular stimulation pulse generator 10 generates stimulation pulses, delivered to the ventricle in the heart 5 via a ventricular lead 8 and a ventricular electrode 9 arranged thereon. The pacemaker can sense the occurrence of physiological events in the heart 5 by sensing cardiac electrical activity. Electrical activity in the atrium is sensed by the atrial electrode 7, and is sent in the form of a raw signal via the lead 6 to the atrial detector 3 from which it is emitted, after certain signal (processing) such as amplification, in the form of an atrial output signal when an event is detected in the atrium. Electrical activity in the ventricle is sensed by the ventricular electrode 9, sent in the form of a raw signal via the lead 8 to the ventricular detector 11 from which it is emitted, after certain signal (processing) such as amplification, in the form of a ventricular output signal when an event is detected in the ventricle. Both the atrial and ventricular output signals are sent to the control device 4 in which they are analyzed by the device according to the invention in a procedure described below for determining whether the atrial output signal was emitted as a response to atrial depolarization. The control device 4, which can consist of a microprocessor, contains e.g. a clock frequency-generating time base generator 30 as shown in FIG. 2, or a clock and a number of logic circuits. The control device 4 synchronizes the different units in the pacemaker 1 with one another and also controls the units on the basis of events detected in the heart 5. Using an external programming unit 13, an operator/physician can check on and change settings in the pacemaker 1. Communication between the pacemaker 1 and the external programming unit 13 is conducted via a telemetry unit 12.

FIG. 2 shows a block diagram of the atrial and ventricular detection channels plus the function blocks which analyze the output signal from the atrial detector 3 and which, according to the invention, emit an identification signal for atrial depolarization.

The atrial channel 20 contains the atrial electrode 7 shown in FIG. 1, the atrial detector 3 also shown in FIG. 1 and an atrial pulse-prolonging circuit 25. The atrial detector 3 is formed by a level detector 21 (or some other kind of detector) and a flip-flop 23. The ventricular channel 40 contains the ventricular electrode 9 shown in FIG. 1, the ventricular detector 10 also shown in FIG. 1 and a ventricular pulse-prolonging circuit 45. The ventricular detector 10 is formed by a level detector 41 (or some other kind of detector) and a flip-flop 43. The output terminal of the level detector 21 in the atrial detector 3 is connected to an input terminal of the flip-flop 23 via the line 22, and the output terminal of the flip-flop 23 is connected via the line 24 to the input terminal of the atrial pulse-prolonging circuit 25. In the ventricular channel 40, corresponding elements 41, 43 and 45 are connected in an analogous manner via lines 42 and 44. The flip-flops 23 and 43 are synchronized with the clock frequency set by the time base generator 30. The flip-flop 23 generates the output signal of the atrial detector 3 on line 24 in the form of an atrial pulse A with a duration, designated a, governed by the sensed event. The atrial pulse-prolonging circuit 25 prolongs the atrial pulse A by an optional value y, so the prolonged atrial pulse emitted on lines 26 and 27 has a total duration of a+y. The flip-flop 43 generates the output signal of the ventricular detector 10 on line 44 in the form of a ventricular pulse V with a duration, designated v, governed by the sensed event. The ventricular pulse-prolonging circuit 45 prolongs the ventricular pulse V by an optional value x so the prolonged ventricular pulse emitted on line 46 has a total duration of v+x. The atrial pulse-prolonging circuit 25 and the ventricular pulse-prolonging circuit 45 jointly form a window generator 50 which generates a time window for events sensed in the heart 5 (FIG. 3C). The window generator 50 is followed by a comparator 60. The comparator 60 is formed by a flip-flop 61, a shift register 62 and a NOR gate 63. The flip-flop 61, one input terminal 66 of which normally has a high level, is connected to the shift register 62 via the line 64, and the shift register 62 has a line 65 connecting the shift register 62 to other logic circuits in the control device 4. The control device 4 is also connected (dashed line) to the reset input terminal of the shift register 62 and, via the NOR gate 63, to the reset input terminal of the flip-flop 61. The length (width) of pulses will be designated below with an index.

Figure 3C:
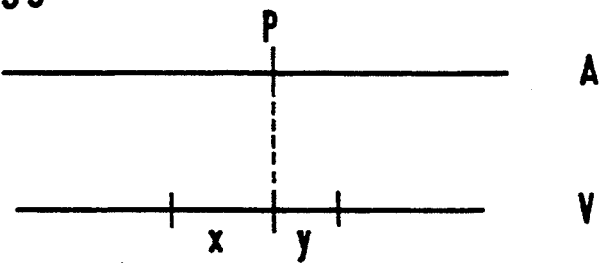
FIG. 3C illustrates the functional time window of the detection device according to the invention.

The function of the device according to FIG. 2 is shown in an overview in FIG. 3A. In FIG. 3A, the time is indicated on the horizontal axis with a scale in which each marking on the axis designates 50 ms. The vertical axis in FIG. 3 indicates signal amplitude without the use of any particular scale and without the amplitude of the signals on different lines shown with a correct inter-signal relationship. The signals shown on the same line on lines 1 and 2 similarly not intended to depict correct inter-signal magnitudes or to jointly encompass all parts of the ECG signal. The object of FIG. 3A is solely to supply an overview of signals important to the invention. On line 1 is shown the electrical activity AE sensed by the atrial electrode 7. On line 2 is shown the electrical activity VE sensed by the ventricular electrode 9. On line 3 is shown the atrial pulses $A_a$ transmitted on line 24 after the flip-flop 23. On line 4 is shown the ventricular pulses $V_v$ transmitted on line 44 after the flip-flop 43. On line 5 is shown the prolonged atrial pulses $A_{a+y}$ transmitted on lines 26, 27 after the atrial pulse-prolonging circuit 25, and on line 6 is shown the prolonged ventricular pulses $V_{v+x}$ on line 46 after the ventricular pulse-prolonging circuit 45. On line 7 is shown the output pulses transmitted on line 64 from the flip-flop 61 in the comparator 60, and on line 8 is shown the identification signals ID for atrial depolarizations transmitted on line 65 after the shift register 62. Finally, on line 9 is shown reset pulses from the control device for the flip-flop 61 and the shift register 62.

When a genuine P wave, e.g. P1 (line 1), is sensed by the atrial electrode 7, the flip-flop 23 generates a pulse $A_a$ with pulse width a. The pulse $A_a$ is prolonged in the pulse-prolonging circuit 25 by a value y, e.g. 10 ms, so the total width of the prolonged atrial pulse $A_{a+y}$ is a+y. The leading edge of the pulse $A_{a+y}$ sets, as designated by the vertical arrow on line 5, the flip-flop 61 in the comparator 60 to a high level by shifting the input terminal 66, which is set to "1" or a high level, so the signal (line 7) arriving at the shift register 62 on line 64 goes high. On the trailing edge of the pulse $A_{a+y}$, received by the shift register 62 via the line 27, the high signal level of the shift register 62 input terminal is sent to line 65, since no electrical activity VE (line 2) occurs in the ventricle during the pulse period $A_{a+y}$, which via the ventricular channel 40, can cause a reset pulse to be sent to the reset input terminal on the flip-flop 61. Thus, the high signal level on line 65 thereby constitutes an identification signal ID for atrial depolarization. The identification signal ID terminates, and the flip-flop 61 and shift register 62 are reset when the reset pulse (line 9) is emitted by the logic in the control device 4.

When a QRS complex, e.g. QRS1 (line 1), is sensed by the atrial electrode 7, the flip-flop 23 again generates an atrial pulse $A_a$, and this pulse is prolonged in the above-described manner into a pulse with the pulse width $A_{a+y}$. However, the QRS complex QRS1 is also sensed by the ventricular electrode 9 (line 2), so the flip-flop 43 generates a ventricular pulse $V_v$ which is prolonged in the pulse-prolonging circuit 45 by a value x, e.g. 20 ms, resulting in a total pulse width of v+x for the pulse $V_{v+x}$. As lines 5 and 6 show, the reset pulse $V_{v+x}$ and the setting pulse $A_{a+y}$ are applied to the respective input terminals of flip-flop 61 with a time overlap so large that the flip-flop 61 cannot be set high by the leading edge of $A_{a+y}$. Thus, the shift register 62 reads a low level for the flip-flop 61 at the negative flank of the pulse $A_{a+y}$, and there is no identification signal ID for atrial depolarization.

The same applies to P2 and QRS2 as was described above for P1 and QRS1. A VES is then sensed, i.e. a ventricular depolarization without a preceding P wave. As FIG. 3A shows, the effect of a VES is the same as for a QRS, i.e. there is no identification signal ID for atrial depolarization. At P3 the atrial electrode 7 again senses a genuine P wave. This wave is identified with an identification signal ID in the same way as described above for P1.

FIG. 3B shows the course of events in detail for the cardiac activities covered by P2, QRS2 and PVC in the overview FIG. 3A. The horizontal axis in FIG. 3B is expanded relative to the horizontal axis in FIG. 3A, although without being related to the latter by a specific scale, since the main object of FIG. 3B is to clearly discriminate components in the functional course.

Detection of a P wave (P2) begins at time $T_1$, leading to a high level for the pulses $A_a$, $A_{a+y}$. As previously noted, the arrow on line 5 indicates that the leading edge of the pulse $A_{a+y}$ sets the signal (line 7) arriving at the shift register 62 high. Detection of the P wave terminates at $T_2$, and the pulse $A_a$ goes low. At $T_3$, i.e. y ms after a concluded P wave, the pulse $A_{a+y}$ goes low, and its trailing edge switches the identification signal ID to a high level (vertical arrow, line 8). A reset pulse (line 9) is emitted by the logic in the control device 4 at $T_4$, the signal on the line 64 and the ID then going low.

At $T_5$ detection of a QRS (QRS2) begins in the ventricle, causing the pulses $V_v$ and $V_{v+x}$ to go high. At $T_6$ detection of QRS2 (far-field) begins in the atrium, causing the pulses $A_a$ and $A_{a+y}$ to go high. At $T_7$ detection of QRS2 ends in the ventricle, and the pulse $V_v$ goes low. At $T_8$, i.e. x ms after $V_v$, $V_{v+x}$ goes low. At $T_9$ detection of QRS2 ends in the atrium, and $A_a$ goes low. At $T_{10}$, i.e., y ms after $A_a$, $A_{a+y}$ goes low. In this process, as previously noted, the pulses $V_{v+x}$ and $A_{a+y}$ have such a time overlap that no identification signal ID can appear.

The course of events for and effect of a VES will be, as noted above, the same as for a QRS, even if, as shown in FIG. 3B, the morphology of a QRS and a PVC differs somewhat. The functional course of events at times $T_{11}$–$T_{16}$ coincides with the course recently described for times $T_5$–$T_{10}$ and need not be repeated here. Thus, no identification signal ID appears with a VES either.

FIG. 3C shows the function of the above-described time window. Detection of an atrial event is always inside the window. A ventricular event detected in the window, i.e. within the period of time x ms before or y ms after detection of the atrial event, makes it impossible for the identification signal ID to appear. However, a missing, or a ventricular event not detected inside the window causes an identification signal ID to appear. The upper part of FIG. 3C shows a detection P on the atrial level A, and the lower part shows the ventricular window x+y on the ventricular level V associated with the atrial detection.

In a subsequent logic circuit arranged in the control device 4, preferably part of the microprocessor in the control device 4, the signals $A_a$ $V_v$ and ID shown in FIG. 3A on lines 3, 4 and 8 are additionally processed to permit identification of the event sensed in the atrium. FIG. 4 shows a flow chart 70 of the additional processing. If an identification signal ID is present, function block 73 determines whether the interval between consecutive identification signals ID (or atrial pulses $A_a$) is shorter or longer than a defined, optional reference interval, e.g. 240 ms. If shorter, block 75 indicates the presence of atrial flutter/fibrillation. If longer, block 74 indicates the presence of P waves with some other rhythm. If no identification signal ID is present, i.e. the pulses $A_a$ (always inside the window) and $V_v$ are both inside the time window, the determination moves to block 76 in the flow chart 70. Block 76 determines whether the interval between consecutive time windows with associated atrial pulses $A_a$ and ventricular pulses $V_v$ is longer or shorter than some other optional interval, e.g. 100 ms (the example 100 ms would correspond to a heart beating at a rate of 600 beats/minute, an improbable rate with normal-frequency QRS complexes). If longer, block 78 indicates the presence of a QRS complex. If shorter, block 77 indicates the presence of interference external to the heart. Block 78 also ascertains whether an identification signal occurs before or after a ventricular event. If before, block 79 indicates the presence of a normal QRS. If after, block 80 indicates the presence of a PVC. It is now apparent that intervals other than those exemplified can be selected with other lengths in order to indicate other conditions in the heart. If desired, block 73 can identify e.g. other kinds of atrial tachycardias, in addition to flutter/fibrillation, when an interval longer than the one constituting the criterion for flutter/fibrillation is imposed.

The circuit logic and/or program flow in the microprocessor in the control device 4 following after the flowchart in FIG. 4 for controlling, on the basis of the indications in blocks 74, 75 and 77, 78, the pulses emitted by the heart stimulator (for treating atrial flutter or bradycardia, for example) are not described herein, since they are not part of the invention and can easily be achieved by one of ordinary skill in the art. Such a person of ordinary skill in the art can also easily achieve modifications of parts shown in the block diagram in FIG. 2. For example, the level detectors 3 and 10 can be replaced, as noted above, with detectors which emit a pulse with a defined duration, independently of the duration of the event.

Although modifications and changes may be suggested by those skilled in the art, it is the intention of the inventor to embody within the patent warranted hereon all changes and modifications as reasonably and properly come within the scope of her contribution to the art.

I claim as my invention:

1. A device for identifying an event, among a plurality of atrially sensed events in a heart, as an atrial depolarization, comprising:
    atrial detector means for emitting a first signal upon the detection of an event in the atrium;
    ventricular detector means for emitting a second signal upon the detection of an event in the ventricle;
    window generator means for generating a time window with said first signal inside said time window; and
    comparator means for comparing said second signal to said time window and for emitting an identification signal indicating atrial depolarization when said second signal is not inside said time window.

2. A device as claimed in claim 1 wherein said atrial detector means comprises means for designating said first signal as an atrial pulse, and wherein said window generator means includes atrial pulse-prolonging circuit means, to which said signal designated as an atrial pulse is supplied, for prolonging said atrial pulse by a defined, selectable value.

3. A device as claimed in claim 1 wherein said ventricular detector means comprises means for designating said second signal as a ventricular pulse, and wherein said window generator means includes ventricular pulse-prolonging means, to which said signal designated as a ventricular pulse is supplied, for prolonging said ventricular pulse by a defined, selectable value.

4. A device as claimed in claim 1 wherein said atrial detector means comprises means for designating said first signal as an atrial pulse and wherein said ventricular detector means comprises means for designating said second signal as a ventricular pulse, and wherein said window generator means includes atrial pulse-prolonging means, to which said signal designated as an atrial pulse is supplied, for prolonging said atrial pulse by a defined, selectable value and ventricular pulse-prolonging means, to which said signal designated as a ventricular pulse is supplied, for prolonging said ventricular pulse by a further defined, selectable value.

5. A device as claimed in claim 4 wherein said means for prolonging said atrial pulse produces a prolonged atrial pulse having a leading edge and a trailing edge and wherein said means for prolonging said ventricular pulse produces a prolonged ventricular pulse, and wherein said comparator means comprises;
   a flip-flop having a signal input to which said prolonged atrial pulse is supplied and a reset input to which said prolonged ventricular pulse is supplied, said flip-flop being capable of assuming a first logic state or a second logic state, said flip-flop assuming said first logic state, if said prolonged ventricular pulse is not received at said reset input, upon the occurrence of said leading edge of said prolonged atrial pulse, and said flip-flop becoming reset to said second logic state if said prolonged ventricular pulse is received at said reset input during the duration of said prolonged atrial pulse; and
   shift circuit means, to which said prolonged atrial pulse is supplied, for reading said state of said flip-flop upon the occurrence of said trailing edge of said prolonged atrial pulse and for emitting said identification signal if said flip-flop is in said first logical state.

6. A device as claimed in claim 1 wherein said atrial detector means detects a plurality of successive events in said atrium and emits a plurality of successive first signals respectively corresponding to said successive events, said device further comprising:
   means, if an identification signal is present, for identifying an interval between consecutive first signals;
   means for designating a first signal as representative of atrial tachyrhythmia if said interval is less than a selected reference interval; and
   means for designating a first signal as representative of a P-wave if said interval is longer than said selected reference interval.

7. A device as claimed in claim 6 wherein said means for designating a first signal as representative of atrial tachyrhythmia comprises means for designating a first signal as representative of atrial flutter/fibrillation if said interval is less than said selected reference interval.

8. A device as claimed in claim 1 wherein said atrial detector means detects a plurality of successive events in said atrium and emits a plurality of successive first signals respectively corresponding to said successive events, said device further comprising:
   means, if an identification signal is present, for identifying an interval between successive identification signals;
   means for designating an identification signal as representative of atrial tachyrhythmia if said interval is less than a selected reference interval; and
   means for designating an identification signal as representative of a P-wave if said interval is longer than said selected reference interval.

9. A device as claimed in claim 8 wherein said means for designating an identification signal as representative of atrial tachyrhythmia comprises means for designating an identification signal as representative of atrial flutter/fibrillation if said interval is less than said selected reference interval.

10. A device as claimed in claim 1 wherein said atrial detector means detects a plurality of successive events in said atrium and emits a plurality of successive first signals respectively corresponding to said successive events, said device further comprising:
    means for designating each of said first signals as an atrial pulse;
    means, if an identification signal is present, for identifying an interval between successive atrial pulses;
    means for designating an atrial pulse as representative of atrial tachyrhythmia if said interval is less than a selected reference interval; and
    means for designating an atrial pulse as representative of a P-wave if said interval is longer than said selected reference interval.

11. A device as claimed in claim 10 wherein said means for identifying an atrial pulse as representative of atrial tachyrhythmia comprises means for identifying an atrial pulse as representative of atrial flutter/fibrillation if said interval is less than said selected reference interval.

12. A device as claimed in claim 1 wherein said atrial detector means and said ventricular detector means respectively emit a plurality of consecutive first and second signals respectively corresponding to consecutive events in said atrium and in said ventricle, said device further comprising:
    means, if no identification signal is present, for identifying an interval between successive time intervals associated to corresponding first and second signals;
    means for designating a first signal as representative of a QRS complex if said interval is longer than a selected reference interval; and
    means for designating a first signal as representative of external interference if said interval is less than said selected reference interval.

13. A device as claimed in claim 12 wherein said means for designating a first signal as representative of a QRS complex comprises means for designating a first signal as representative of a normal QRS complex if an identification signal occurs before a next second signal is emitted and for designating a first signal as representative of a PVC if an identification signal occurs after a next second signal is emitted.

14. A device as claimed in claim 1 wherein said atrial detector means and said ventricular detector means respectively emit a plurality of consecutive first and second signals respectively corresponding to consecutive events in said atrium and in said ventricle, said device further comprising:
    means for designating each first signal as an atrial pulse;
    means for designating each second signal as a ventricular pulse;
    means, if no identification signal is present, for identifying time intervals between successive time windows associated with corresponding atrial and ventricular pulses;
    means for designating an atrial pulse as representative of a QRS complex if said interval is lower than a selected reference interval; and
    means for designating an atrial pulse as representative of external interference if said interval is less than said selected reference interval.

15. A device as claimed in claim 14 wherein said means for designating an atrial pulse as representative of a QRS complex comprises means for designating an atrial pulse as a normal QRS complex if an identification signal occurs before said atrial pulse and for designating an atrial pulse as representative of a VES if an identification signal occurs after said atrial pulse.

16. A device as claimed in claim 1, further comprising:
   means for stimulating a heart at a stimulation rate; and
   control means for controlling said stimulation rate of said means for stimulating dependent on the occurrence of said identification signal.

17. A method for identifying an event, among a plurality of atrially sensed events in a heart, as an atrial depolarization, comprising the steps of:
   emitting a first signal upon the detection of an event in the atrium;
   emitting a second signal upon the detection of an event in the ventricle;
   generating a time window with said first signal inside said time window; and
   comparing said second signal to said time window and for emitting an identification signal indicating atrial depolarization when said second signal is not inside said time window.

18. A method as claimed in claim 17 comprising the additional steps of:
   designating said first signal as an atrial pulse; and
   prolonging said atrial pulse by a defined, selectable value.

19. A method as claimed in claim 17 comprising the additional steps of:
   designating said second signal as a ventricular pulse; and
   prolonging said ventricular pulse by a defined, selectable value.

20. A method as claimed in claim 17 comprising the additional steps of:
   designating said first signal as an atrial pulse;
   designating said second signal as a ventricular pulse;
   prolonging said atrial pulse by a defined, selectable value; and
   prolonging said ventricular pulse by a further defined, selectable value.

21. A method as claimed in claim 20 wherein the steps of prolonging said atrial pulse produces a prolonged atrial pulse and wherein the steps of for prolonging said ventricular pulse produces a prolonged ventricular pulse, and wherein the steps of emitting said identification signal is further defined by emitting said identification signal if said prolong ventricular pulse does not overlap said prolonged atrial pulse.

22. A method as claimed in claim 17 wherein the step of emitting a first signal is further defined by detecting a plurality of successive events in said atrium and emitting a plurality of successive first signals respectively corresponding to said successive events, said method comprising the additional steps of:
   if an identification signal is present, identifying an interval between consecutive first signals;
   designating a first signal as representative of atrial tachyrhythmia if said interval is less than a selected reference interval; and
   designating a first signal as representative of a P-wave if said interval is longer than said selected reference interval.

23. A method as claimed in claim 22 wherein the steps of designating a first signal as representative of atrial tachyrhythmia is further defined by designating a first signal as representative of atrial flutter/fibrillation if said interval is less than said selected reference interval.

24. A method as claimed in claim 17 wherein the step of emitting a first signal is further defined by detecting a plurality of successive events in said atrium and emitting a plurality of successive first signals respectively corresponding to said successive events, said method comprising the additional steps of:
   if an identification signal is present, identifying an interval between successive identification signals;
   designating an identification signal as representative of atrial tachyrhythmia if said interval is less than a selected reference interval; and
   designating an identification signal as representative of a P-wave if said interval is longer than said selected reference interval.

25. A method as claimed in claim 24 wherein the steps of identifying an identification signal as representative of atrial tachyrhythmia is further defined by designating an identification signal as representative of atrial flutter/fibrillation if said interval is less than said selected reference interval.

26. A method as claimed in claim 17 wherein the steps of emitting a first signal is further defined by detecting a plurality of successive events in said atrium and emitting a plurality of successive first signals respectively corresponding to said successive events, said method further comprising the additional steps of:
   designating each of said first signals as an atrial pulse;
   if an identification signal is present, identifying an interval between successive atrial pulses;
   designating an atrial pulse as representative of atrial tachyrhythmia if said interval is less than a selected reference interval; and
   designating an atrial pulse as representative of a P-wave if said interval is longer than said selected reference interval.

27. A method as claimed in claim 26 wherein the step of designating an atrial pulse as representative of atrial tachyrhythmia is further defined by designating an atrial pulse as representative of atrial flutter/fibrillation if said interval is less than said selected reference interval.

28. A method as claimed in claim 17 wherein the steps of emitting said first and second signals are further defined by emitting a plurality of consecutive first and second signals respectively corresponding to consecutive events in said atrium and in said ventricle, said method comprising the additional steps of:
   if no identification signal is present, identifying an interval between successive time intervals associated with corresponding first and second signals;
   designating a first signal as representative of a QRS complex if said interval is lower than a selected reference interval; and
   designating a first signal as representative of external interference if said interval is less than said selected reference interval.

29. A method as claimed in claim 28 wherein the step of designating a first signal as representative of a QRS complex is further defined by designating a first signal as representative of a normal QRS complex if an identification signal occurs before said first signal is emitted and designating a first signal as representative of a VES if an identification signal occurs after said first signal is emitted.

30. A method as claimed in claim 17 wherein the steps of emitting said first and second signals are further defined by emitting a plurality of consecutive first and second signals respectively corresponding to consecutive events in said atrium and in said ventricle, said method comprising the additional steps of:

designating each first signal as an atrial pulse;

designating each second signal as a ventricular pulse;

if no identification signal is present, identifying time intervals between successive time windows associated with corresponding atrial and ventricular pulses;

designating an atrial pulse as representative of a QRS complex if said interval is longer than a selected reference interval; and designating an atrial pulse as representative of external interference if said interval is less than said selected reference interval.

31. A method as claimed in claim 30 wherein the step of designating an atrial pulse as representative of a QRS complex is further defined by designating an atrial pulse as a normal QRS complex if an identification signal occurs before said atrial pulse and designating an atrial pulse as representative of a VES if an identification signal occurs after said atrial pulse.

32. A method as claimed in claim 17, comprising the additional steps of:

stimulating a heart at a stimulation rate; and controlling said stimulation rate dependent on the occurrence of said identification signal.

* * * * *